(12) United States Patent
'T Hooft et al.

(10) Patent No.: US 10,551,170 B2
(45) Date of Patent: Feb. 4, 2020

(54) FIBER OPTIC SENSORS FOR DETERMINING 3D SHAPE

(75) Inventors: Gert Wim 'T Hooft, Eindhoven (NL); Robert Manzke, Sleepy Hollow, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1095 days.

(21) Appl. No.: 13/981,692

(22) PCT Filed: Jan. 23, 2012

(86) PCT No.: PCT/IB2012/050295
§ 371 (c)(1),
(2), (4) Date: Jul. 25, 2013

(87) PCT Pub. No.: WO2012/101562
PCT Pub. Date: Aug. 2, 2012

(65) Prior Publication Data
US 2013/0308138 A1    Nov. 21, 2013

Related U.S. Application Data

(60) Provisional application No. 61/437,192, filed on Jan. 28, 2011.

(51) Int. Cl.
    *G01B 11/24*    (2006.01)
    *G01B 11/16*    (2006.01)
    *A61B 34/20*    (2016.01)
(52) U.S. Cl.
    CPC .............. *G01B 11/24* (2013.01); *A61B 34/20* (2016.02); *G01B 11/18* (2013.01); *A61B 2034/2061* (2016.02)
(58) Field of Classification Search
    CPC ......... G01N 21/25; G01J 11/24; G01B 11/24; G01B 11/18
    (Continued)

(56) References Cited

U.S. PATENT DOCUMENTS

| 4,806,012 A | 2/1989 | Meltz et al. |
| 4,950,883 A | 8/1990 | Glenn |

(Continued)

FOREIGN PATENT DOCUMENTS

| CN | 1595056 A | 3/2005 |
| CN | 101226051 A | 7/2008 |

(Continued)

OTHER PUBLICATIONS

G. Flockhart et al., "Differential Phase Tracking Applied to Bragg Gratings in Mulei-Core Fibre for High Accuracy Curvature Measurement", Electronics Letters, IEE Stevenge, GB, vol. 42, No. 7, Mar. 30, 2006, pp. 390-391.

(Continued)

*Primary Examiner* — Rebecca C Bryant

(57) ABSTRACT

An optical shape sensing system employing an elongated device, an optical fiber embedded within the elongated device with the optical fiber, an optical interrogation console and a 3D shape reconstructor. In operation, the optical interrogation console generates reflection spectrum data indicative of a measurement of both an amplitude and a phase of a reflection for each core of the optical fiber as a function of wavelength. The 3D shape reconstructor executes a generation of local strain data for a plurality of positions along the optical fiber responsive to the reflection spectrum data, a generation of local curvature and torsion angle data as a function of each local strain along the fiber, and a reconstruction of the 3D shape of the optical fiber as a function of each local curvature and torsion angle along the optical fiber.

15 Claims, 4 Drawing Sheets

(58) Field of Classification Search
USPC .............. 356/241.1–241.6, 601, 124–126;
250/227.16, 227.18
See application file for complete search history.

(56) References Cited

U.S. PATENT DOCUMENTS

| | | | |
|---|---|---|---|
| 5,641,956 A | 6/1997 | Vengsarkar et al. | |
| 5,798,521 A * | 8/1998 | Froggatt | G01D 5/35383 250/227.14 |
| 2004/0165178 A1 | 8/2004 | Clements | |
| 2009/0324161 A1 * | 12/2009 | Prisco | G01L 1/246 385/13 |
| 2012/0069347 A1 * | 3/2012 | Klein | G01B 11/161 356/477 |

FOREIGN PATENT DOCUMENTS

| | | |
|---|---|---|
| GB | 2371361 A | 7/2002 |
| WO | WO200133165 | 5/2001 |

OTHER PUBLICATIONS

M. Froggatt et al., "High-Spatial-Resolution Distributed Strain Measurement in Optical Fiber With Rayleigh Scatter", Applied Optics, vol. 37, No. 10, Apr. 1, 1998, pp. 1735-1740.
S. Huang et al., "Continuous Arbitrary Strain profile Measurements with Fiber Bragg Gratings", Smart Materials and Structures, IOP Publishing Ltd., Bristol, GB, vol. 7, No. 2, Apr. 1, 1998, pp. 248-256.
X. Yi et al., "An Innovative 3D Colonoscope Shape Sensing Sensor Based on FBG Sensor Array", Proceedings of the 2007 International Conference on Information Acquisition, Jul. 9-11, 2007, Jeju City, Korea, pp. 227-232.

\* cited by examiner

FIBER OPTIC SENSORS FOR DETERMINING 3D SHAPE

CROSS-REFERENCE TO PRIOR APPLICATIONS

This application is the U.S. National Phase application under 35 U.S.C. § 371 of International Application Serial No. PTC/IB2012/050295, filed on Jan. 23, 2012, which claims the benefit of U.S. Application Ser. No. 61/437,192, filed on Jan. 28, 2011. These applications are hereby incorporated by reference herein.

The present invention generally relates to optical tracking of elongated devices, particularly medical devices (e.g., endoscopes, catheters and guidewires). The present invention specifically relates a three-dimensional ("3D") shape reconstruction of an optical fiber embedded within an elongated device.

The art of shape reconstruction of a multi-core fiber generally involves three (3) steps.

The first step involves a multi-core fiber being interrogated with optical frequency domain reflectometry, which results in the measurement of both an amplitude and a phase of a reflection for each core as a function of wavelength. The reflection may be invoked by embedded periodical structures (e.g., fiber Bragg gratings) or by non-periodic, random variations in the refractive index (e.g., Rayleigh scattering).

The second step involves a calculation of strain in each core at multiple positions along the fiber from the reflection spectra.

The third step involves a 3D shape reconstruction of the optical fiber by means of combining the various strain data. In particular, the strain measurements may be converted to rotation angles and the associated rotation matrices may be used to update a tangent vector, a normal vector and a binormal vector (i.e. columns of a Jacobian matrix). However, the art fails to address how the line elements of the fiber are calculated or how the matrix for converting the strain measurements is established.

The present invention overcomes the inaccuracies in known methods for calculating local curvature and torsion from local values of strain in a multi-core fiber embedded in an elongated device, and for subsequently using this information to evaluate the 3D shape of the elongated device.

One form of the present invention is an optical shape sensing system employing an elongated device, an optical fiber embedded within the elongated device with the optical fiber including one or more cores, an optical interrogation console and a 3D shape reconstructor. In operation, the optical interrogation console generates reflection spectrum data indicative of a measurement of both an amplitude and a phase of a reflection for each core of the optical fiber as a function of wavelength and the 3D shape reconstructor reconstructs a 3D shape of the optical fiber. The 3D shape reconstructor executes a generation of local strain data for a plurality of positions along the optical fiber responsive to the reflection spectrum data, a generation of local curvature and torsion angle data as a function of each local strain along the fiber, and a reconstruction of the 3D shape of the optical fiber as a function of each local curvature and torsion angle along the optical fiber.

The foregoing form and other forms of the present invention as well as various features and advantages of the present invention will become further apparent from the following detailed description of various exemplary embodiments of the present invention read in conjunction with the accompanying drawings. The detailed description and drawings are merely illustrative of the present invention rather than limiting, the scope of the present invention being defined by the appended claims and equivalents thereof.

Figure 1:
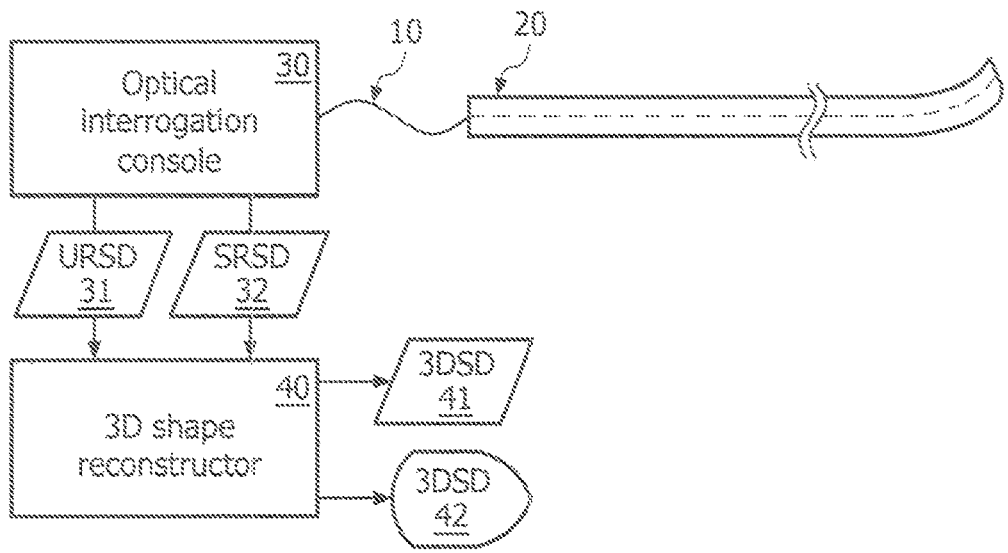
FIG. 1 illustrates a block diagram of an exemplary embodiment of an optical shape sensing system in accordance with the present invention.

As shown in FIG. 1, an optical shape sensing system of the present invention employs an optical fiber 10 embedded within an elongated device 20.

In practice, optical fiber 10 may be any type of optical fiber suitable for optically tracking elongated device 20. Examples of optical fiber 10 include, but are not limited to, a flexible optically transparent glass or plastic fiber incorporating an array of fiber Bragg gratings integrated along a length of the fiber as known in the art, and a flexible optically transparent glass or plastic fiber having naturally variations in its optic refractive index occurring along a length of the fiber as known in the art (e.g., a Rayleigh scattering based optical fiber). Optical fiber 10 may be a single core fiber or preferably, a multi-core fiber.

In practice, elongated device 20 may be any type of device suitable for embedding an optical fiber 10 therein for purposes of optically tracking elongated device 20. Examples of elongated device 20 include, but are not limited to, an endoscope, a catheter and a guidewire.

Still referring to FIG. 1, the system further employs an optical interrogation console 30 and a 3D shape reconstructor 40.

In practice, optical interrogation console 30 may be any device or system structurally configured for transmitting light to optical fiber 10 and receiving reflected light from optical fiber 10. In one embodiment, optical interrogation console 30 employs an optical frequency domain reflectometer and other appropriate electronics/devices as known in the art.

For purposes of the present invention, 3D shape reconstructor 40 is broadly defined herein as any device or system structurally configured for translating measured reflection spectra data of optical fiber 10 into a 3D shape of optical fiber 10 and elongated device 20.

A description of a flowchart 50 representative of an optical shape sensing method of the present invention will now be described herein to facilitate a more detailed understanding of 3D shape reconstructor 40.

Figure 2:
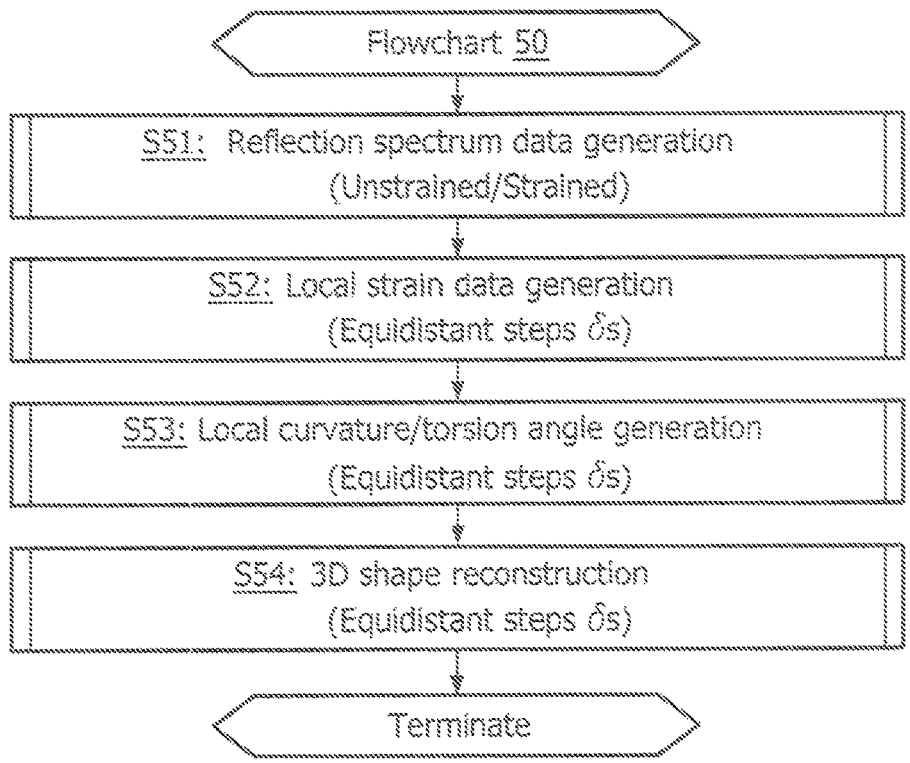
FIG. 2 illustrates a flowchart representative of an exemplary embodiment of an optical shape sensing method in accordance with the present invention.

Referring to FIG. 2, a stage S51 of flowchart 50 encompasses optical interrogation console 30 generating unstrained reflection spectrum data ("URSD") 31 indicative of a measurement of both an amplitude and a phase of a reflection for each core of optical fiber 10 as a function of wavelength when optical fiber 10 is in a reference shape. In addition, optical interrogation console 30 generating strained reflection spectrum data ("SRSD") 32 indicative of a measurement of both an amplitude and a phase of a reflection for each core of optical fiber 10 as a function of wavelength when optical fiber 10 is in a non-reference shape.

For purposes of the present invention, the term "reference shape" is broadly defined herein as a designated shape of optical fiber 10 whereby optical fiber 10 may or may not be experiencing any degree of strain along various positions of optical fiber 10, but for shape reconstruction purposes is assumed to be experiencing a baseline strain relative to any other shape of optical fiber 10. Conversely, the term "non-reference shape" is broadly defined herein as any shape of optical fiber 10 other than the reference shape.

In one embodiment, optical interrogation console 30 implements an optical frequency domain reflectometry as known in the art for generating reflection spectrum data 31 and 32.

Optical interrogation console 30 communicates reflection spectrum data 31 and 32 to 3D shape reconstructor 40, which processes reflection spectrum data 31 and 32 for generating local strain data as a function of position along optical fiber 30 during a stage S52 of flowchart 50.

In one embodiment of stage S52 for a fiber Bragg grating based optical fiber 10, 3D shape reconstructor 40 generates the local strain .epsilon. by a simple Fourier transform of both reflection spectrum data 31 and 32. Specifically, the reflection spectrum is known from data 31 and 32. As such, a taper function $\Omega e^{i\Phi}$ is calculated whereby a spatial dependence of a phase of the taper function $\Omega e^{i\Phi}$ is a measure for the local strain .epsilon. in accordance with the following equations [1]-[3]:

$$\delta = \frac{2\pi n}{\lambda} - \frac{\pi}{\Lambda} \quad [1]$$

$$\Omega(s) \cdot e^{i\varphi(s)} = i \int_{-\infty}^{+\infty} \sigma(\delta) e^{i 2\delta s} d\delta \quad [2]$$

$$\frac{d\varphi}{ds} = -\frac{2\pi p}{\Lambda} \cdot \varepsilon \quad [3]$$

where $\delta$ is the detuning (i.e., the difference of the wave vector from the central resonance peak), $\lambda$ is the wavelength of the light, n is the effective refractive index of the mode, $\Lambda$ is the periodicity of the Bragg grating, quantity p is a calibration constant (e.g., 0.78 for a single mode fiber based on quartz), and $\sigma(\delta)$ is the complex valued Fresnel reflection coefficient.

Both reflection spectrum data 31 and 32 are inverse Fourier transformed in accordance with equation [2] whereby a magnitude $\Omega$ of the taper function is unaltered in view of data 31 and 32 being generated from the same optical fiber 10. A phase $\varphi$ of the taper function, however, does change between two transforms whereby a difference of the two (2) phase curves is calculated and the slope of this phase difference as a function of position on the fiber is evaluated. Equation [3] is used thereafter to generate the local strain $\varepsilon$ as a function of position on the fiber.

In an alternative embodiment of stage S52, the inverse Fourier transforms of equation [2] of reflection spectrum data 31 and 32 are also calculated. However, a part of the taper function at a particular distance s is taken, and again back Fourier transformed. In this way, only the reflection spectrum at that distance s is obtained. This local reflection spectrum is compared with the local reflection spectrum of the unstrained fiber by calculating their cross correlation. The cross correlation exhibits a peak, its position is the detuning shift of the two local spectra. The relative wavelength shift is directly proportional to the local strain $\varepsilon$ with proportionality constant p.

In practice for stage S52 in accordance with either embodiment, the Fourier transform(s) of the reflection spectrum data 31 and 32 may be taken at equidistant detuning steps whereby the local strains $\varepsilon$ are known at equidistant steps $\delta s$ along length of optical fiber 10.

Still referring to FIG. 2, a stage S53 of flowchart 50 encompasses 3D shape reconstructor 40 generating a local curvature and integral of torsion as function of fiber position.

Figure 3:
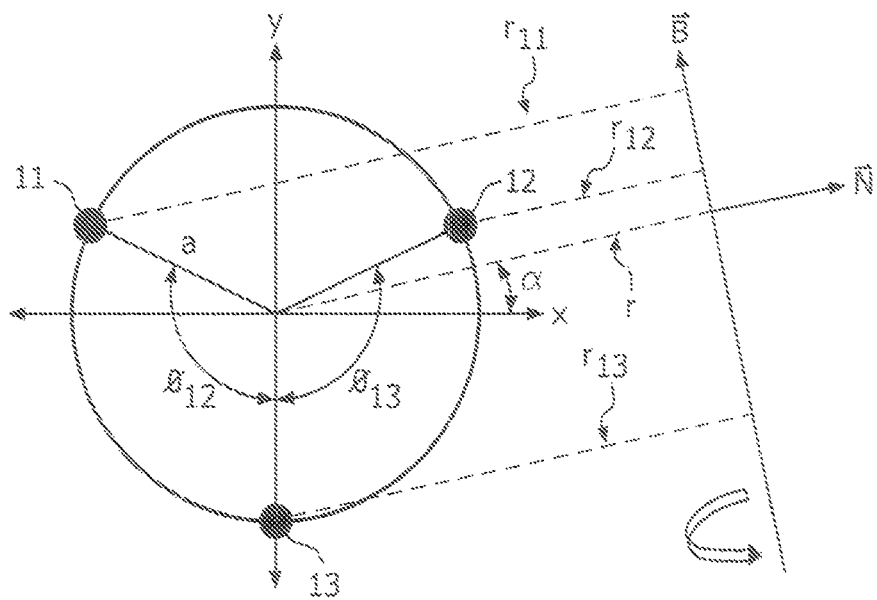
FIGS. 3 and 4 illustrate views of a 3D shape reconstruction of an optical fiber in accordance with the present invention.

In one embodiment of stage S53 for a three (3) cores 11-13 of optical fiber 10 as shown in FIG. 3, the following equations [4]-[6] are executed for local curvature κ and torsion angle τ:

$$\tan(\alpha) = \frac{\varepsilon_{12} \cdot \sin(\phi_{13}) + \varepsilon_{13} \cdot \sin(\phi_{12})}{\varepsilon_{12} \cdot (\cos(\phi_{13}) - 1) - \varepsilon_{13} \cdot (\cos(\phi_{12}) - 1)} \quad [4]$$

$$\kappa = \frac{\varepsilon_{12}}{a \cdot [\sin(\alpha + \phi_{12}) - \sin(\alpha)]} \quad [5]$$

$$\tau = \frac{d\alpha}{ds} \quad [6]$$

where $\varepsilon_{12} = \varepsilon_2 - \varepsilon_1$ and $\varepsilon_{13} = \varepsilon_3 - \varepsilon_1$.

Furthermore, torsion is a rotation around the tangent whereby torsion causes the curve to change its plane of curvature. This means that torsion changes the direction of the axis B of the rotation associated with curvature. In other words torsion gives rise to a change in the angle α, hence the name torsion angle.

Upon completion of stage S53, 3D shape reconstructor 40 has generated equidistant values for local curvature κ and torsion angle τ.

Still referring to FIG. 2, a stage S54 of flowchart 50 comprises 3D shape reconstructor 40 reconstructing a shape of optical fiber 10 and elongated device 20 as a function of the local curvatures κ and torsion angles τ.

In one embodiment of stage S54, the approach is to evaluate the 3D shape of a curve by starting at the one end of the curve (e.g., s=0). With this approach, the absolute position r(x,y,z) in local space and the tangent should be given as boundary conditions. The next position $\delta s$ further down optical fiber 10 is calculated using the curvature and torsion angle of the previous point. Also, the notion, that curvature is a rotation around the binormal vector B is applied to perform this step.

Figure 4:
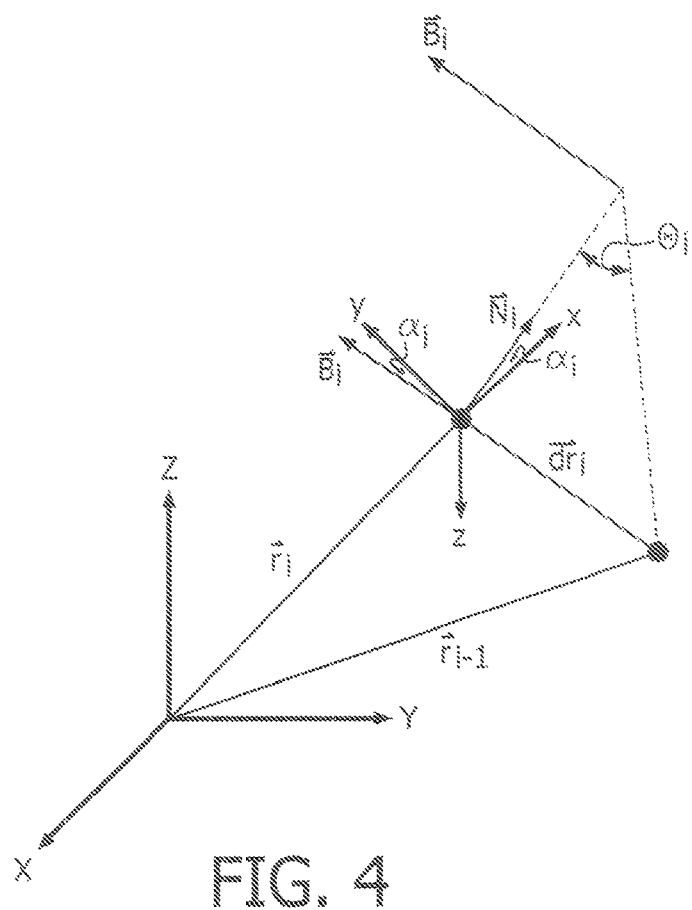

For example, FIG. 4 shows a position $r_i$ from which the next position $r_{i+1}$ has to be calculated. There are two coordinate systems: a fixed reference frame (X,Y,Z) and a local coordinate system (x',y',z') that rotates and translates along with the curve. The elementary step length $\delta s$ is a small line segment of a circle with radius $1/\kappa_i$. The angle associated with the line segment is $\theta_i = \delta s \cdot \kappa_i$. A chord of this circle segment must be calculated. The two radii that encompass the circle segment have the direction of $\vec{N}$ and $\overline{R}(\theta, \vec{B}) \cdot \vec{N}$. Where $\overline{R}(\theta, \vec{B})$ signifies the rotation around the binormal vector over angle θ. In the local coordinate system, the chord is given by the following equation [7]:

$$d\vec{r}_i' = \frac{1}{\kappa_i} \vec{N}_i - \frac{1}{\kappa_i} \overline{R}(\theta_i, \vec{B}_i) \cdot \vec{N}_i \quad [7]$$

The coordinate system $(x_i', y_i', z_i')$ and (X,Y,Z) are simply related by a Jacobian matrix $A_i$. This matrix is a unitary matrix whereby the first Jacobian matrix at the begin point is given by the boundary conditions. So, the chord for the next point may be calculated with the Jacobian matrix of the previous point as long as this matrix is updated appropriately. Therefore, the new position in the laboratory frame can be obtained by the following equation [8]:

$$\vec{r}_{i+1} = \vec{r}_i + \frac{1}{\kappa_i}\bar{\bar{A}}_i \cdot \left(\bar{\bar{I}} - \bar{\bar{R}}(\theta_i, \vec{B}_i)\right) \cdot \vec{N}_i \quad [8]$$

An update of the Jacobian matrix is straightforward. The local coordinate system (x',y',z') at the next point is rotated over the same angle θ along the same binormal axis. Consequently, the following equation [9] provides $$\bar{\bar{A}}_{i+1} = \bar{\bar{A}}_i \cdot \bar{\bar{R}}(\theta_i, \vec{B}_i) \quad [9]$$

Referring to FIGS. 1 and 2, stages S51-S54 are continually repeated during the course of optically tracking elongated device 20. With each shape reconstruction of optical fiber 10 and elongated device 20 of stage S54, 3D shape reconstructor may provide 3D shape data ("3DSD") 41 to any appropriate tracking device and/or 3D shape display ("3DSD") 42 to display the shape reconstruction of optical fiber 10 and elongated device 20.

Flowchart 50 has been tested for various cases. For example, in one test case, an optical fiber with a helical form having a length of one (1) meter was tested based 6,500 number of data points along the fiber. The helix had a radius of curvature of ten (10) cm and a pitch of 6.3 cm, meaning that the torsion is 1 m$^{-1}$. The fiber contained three cores separated from the center by fifty (50) microns. Each of the cores contained thirty-eighth (38) fiber Bragg gratings with a length of approximately twenty-five (25) mm, and separated by gaps of about one (1) mm in size.

Figure 5:
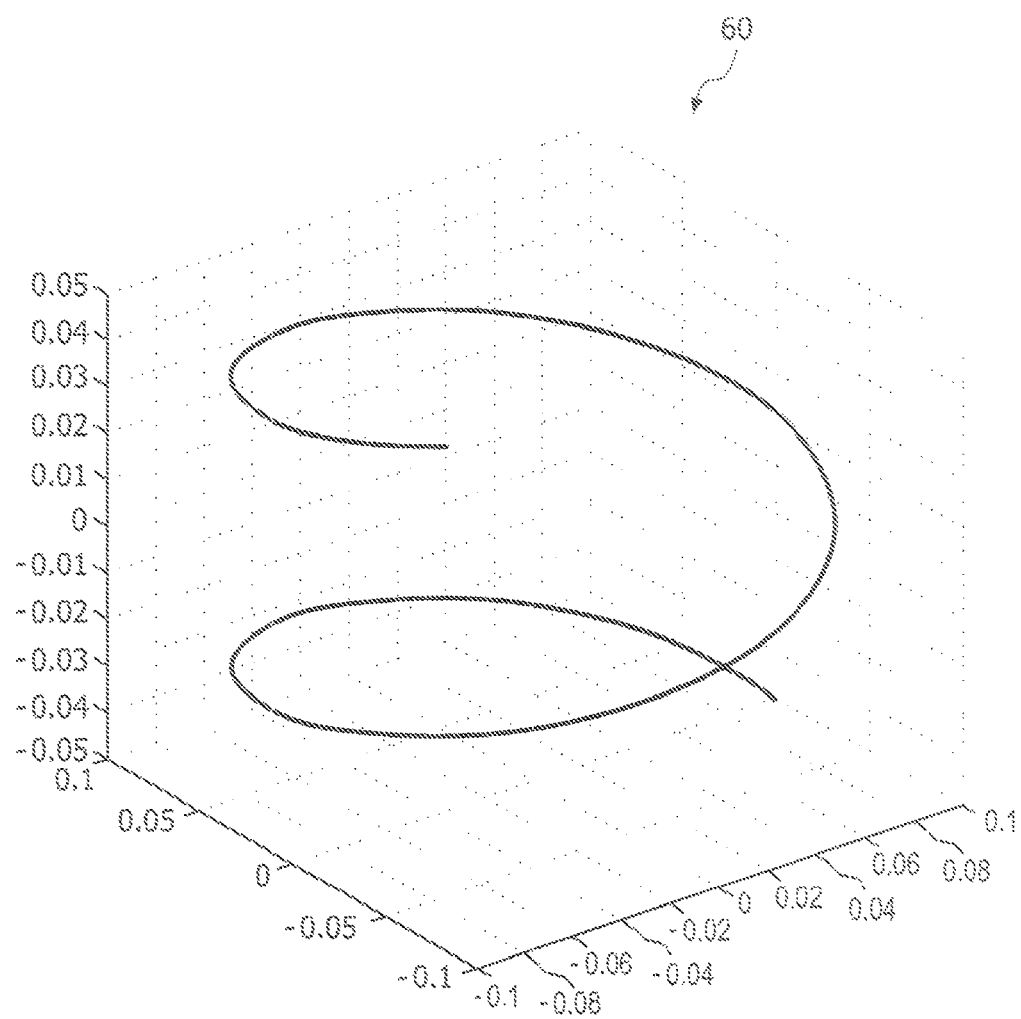
FIG. 5 illustrates a comparison of actual data and shape reconstruction data in accordance with the present invention.
Figure 6:
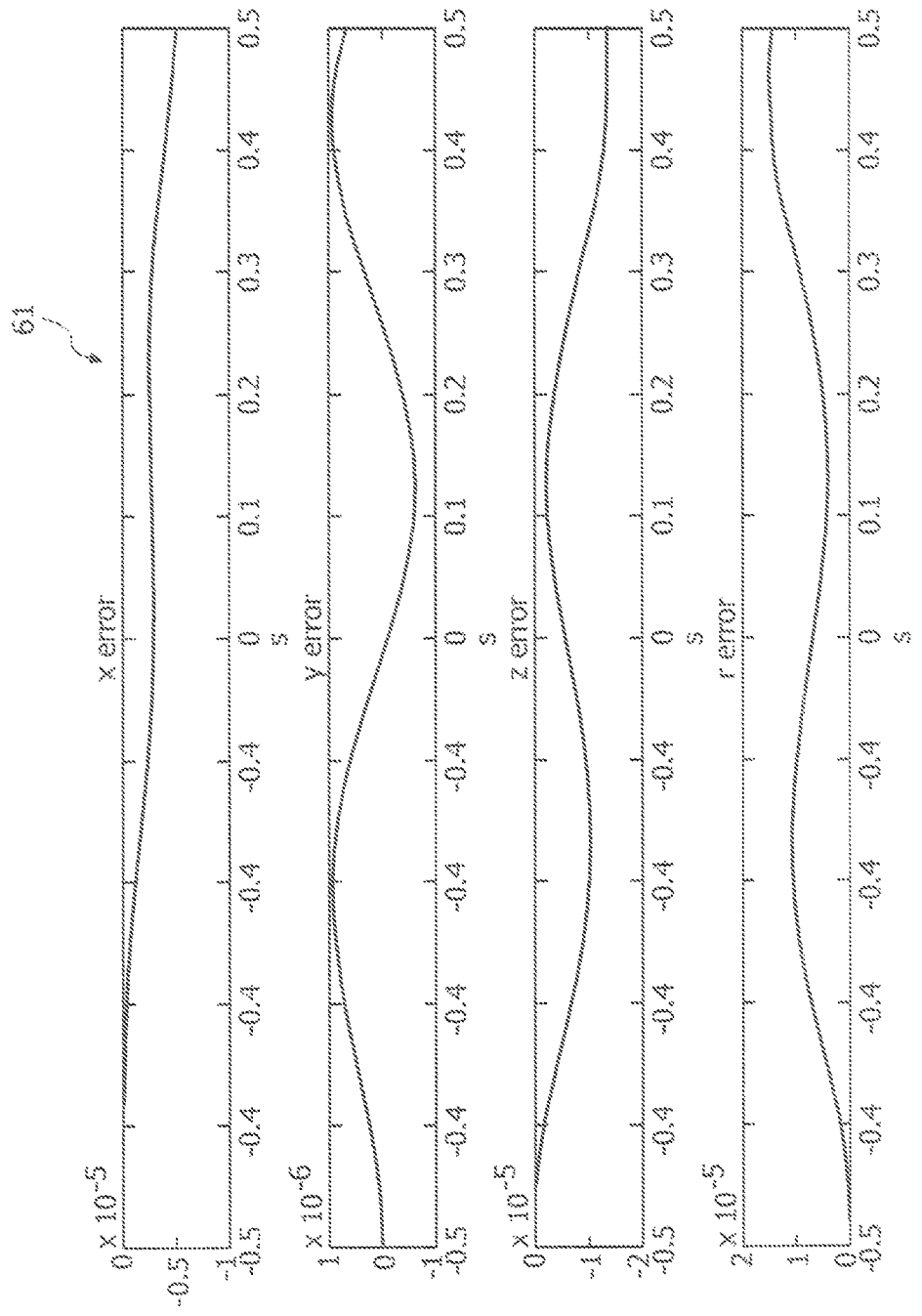
FIG. 6 illustrates deviation graphs in accordance with the present invention.

FIG. 5 illustrates a graph 60 showing the original form of the helix and the reconstructed data with significant overlap in view of the fact that the original data and the reconstructed data cannot be distinguished from one another on the scale of this graph 60. FIG. 6 illustrates a graph 61 showing deviations between the original data and the reconstructed data of FIG. 5. Specifically, the small deviations oscillate with the pitch of the helix and the total error in the reconstruction is of the order of ten (10) microns over one (1) meter of fiber length. For most applications, the accuracy is more than sufficient.

From the description of FIGS. 1-6, those having ordinary skill in the art will have a further appreciation how to implement the 3D shape reconstruction technique for an optical fiber in accordance with the present invention for numerous applications, particularly for the optical tracking of elongated medical devices (e.g., endoscopes, catheters and guidewires). Examples of medical applications include, but are not limited to, EP ablation procedures, and interventions in coronary arteries (e.g., stent placement) in-situ fenestration while performing stent graft placement for aortic abdominal aneurysms and positioning of ultrasound probes.

While various exemplary embodiments of the present invention have been illustrated and described, it will be understood by those skilled in the art that the exemplary embodiments of the present invention as described herein are illustrative, and various changes and modifications may be made and equivalents may be substituted for elements thereof without departing from the true scope of the present invention. For example, although the invention is discussed herein with primarily with regard to FBGs, it is understood to include fiber optics for shape sensing or localization generally, including, for example, with or without the presence of FBGs or other optics, sensing or localization from detection of variation in one or more sections in a fiber using back scattering, optical fiber force sensing, fiber location sensors or Rayleigh scattering. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. An optical shape sensing system, comprising:
   an elongated device;
   an optical fiber embedded within the elongated device, the optical fiber including at least one core;
   an optical interrogation console in communication with the optical fiber for generating reflection spectrum data indicative of a measurement of both an amplitude and a phase of a reflection for each core of the optical fiber as a function of wavelength, wherein the reflection spectrum data includes
      unstrained reflection spectrum data indicative of a measurement of both the amplitude and the phase of the reflection for each core of the optical fiber as the function of wavelength in response to optical fiber having a reference shape; and
      strained reflection spectrum data indicative of a measurement of both the amplitude and the phase of the reflection for each core for the optical fiber as the function of wavelength in response to optical fiber having a non-reference shape; and
   a 3D shape reconstructor in communication with the optical interrogation console for reconstructing a 3D shape of the optical fiber;
      wherein the 3D shape reconstructor is structurally configured, responsive to the reflection spectrum data, to generate local strain data for each position of a plurality of positions along the optical fiber,
      wherein a generation of the local strain data includes an execution of inverse Fourier transforms of the reference reflection spectrum data and the reflection spectrum data with additional strain,
      wherein the generation of the local strain data further includes a calculation of a phase difference between taper functions corresponding to the inverse Fourier transforms of the unstrained reflection spectrum data and the strained spectrum data,
      wherein the 3D shape reconstructor is further structurally configured, responsive to the local strain data, to generate local curvature and torsion angle data at each position of the plurality of positions along the optical fiber as a function of corresponding local strain at each position of the plurality of positions along the optical fiber, and
      wherein the 3D shape reconstructor is further structurally configured, responsive to the local curvature and torsion angle data, to reconstruct the 3D shape of the optical fiber as a function of the local curvature and torsion angle at each position of the plurality of positions along the optical fiber.

2. The optical shape sensing system of claim 1, wherein the elongated device is selected from a group including an endoscope, a catheter and a guidewire.

3. The optical shape sensing system of claim 1, wherein the optical fiber includes at least three cores.

4. The optical shape sensing system of claim 1, wherein the optical interrogation console includes an optical frequency domain reflectometer.

5. The optical shape sensing system of claim 1, wherein a generation of the local strain data includes an execution of an inverse Fourier transform of the reflection spectrum data.

6. An optical shape sensing system, comprising:
an elongated device;
an optical fiber embedded within the elongated device, the optical fiber including at least one core;
an optical interrogation console in communication with the optical fiber for generating reflection spectrum data indicative of a measurement of both an amplitude and a phase of a reflection for each core of the optical fiber as a function of wavelength, wherein the reflection spectrum data includes
unstrained reflection spectrum data indicative of a measurement of both the amplitude and the phase of the reflection for each core of the optical fiber as the function of wavelength in response to optical fiber having a reference shape, and
strained reflection spectrum data indicative of a measurement of both the amplitude and the phase of the reflection for each core of the optical fiber as the function of wavelength in response to optical fiber having a non-reference shape; and
a 3D shape reconstructor in communication with the optical interrogation console for reconstructing a 3D shape of the optical fiber,
wherein the 3D shape reconstructor is structurally configured, responsive to the reflection spectrum data, to generate local strain data for a plurality of positions along the optical fiber,
wherein the 3D shape reconstructor is further structurally configured, responsive to the local strain data, to generate local curvature and torsion angle data as a function of each local strain along the optical fiber, and
wherein the 3D shape reconstructor is further structurally configured, responsive to the local curvature and torsion angle data, to reconstruct the 3D shape of the optical fiber as a function of the local curvature and torsion angle along the optical fiber,
wherein a generation of the local strain data includes an execution of inverse Fourier transforms of the reference reflection spectrum data and the reflection spectrum data with additional strain; and
wherein the generation of the local strain data further includes a calculation of a phase difference between taper functions corresponding to the inverse Fourier transforms of the unstrained reflection spectrum data and the strained reflection spectrum data.

7. The optical shape sensing system of claim 1, wherein the generation of the local strain data further includes a cross-correlation of an inverse Fourier transforms of the unstrained reflection spectrum data and the strained reflection spectrum data.

8. The optical shape sensing system of claim 1, wherein each position is equidistant along the optical fiber.

9. The optical shape sensing system of claim 1, wherein the reconstruction of the 3D shape of the optical fiber includes a step size rotation of a local binormal axis of a curve over an angle equaling a product of the step size and curvature.

10. The optical shape sensing system of claim 9, wherein the reconstruction of the 3D shape of the optical fiber further includes a coordinate transformation of a local coordinate system to a reference coordinate system.

11. The optical shape sensing system of claim 10, wherein the reconstruction of the 3D shape of the optical fiber further includes a calculation of a Jacobian matrix of the coordinate transformation for each step using the same rotation.

12. The optical shape sensing system of claim 1, wherein the 3D shape reconstructor is operable to generate at least one of 3D reconstruction data for external use and a 3D reconstruction display of the optical fiber.

13. An optical shape sensing method for an optical fiber embedded within an elongated device, the optical fiber including at least one core, the optical shape sensing method comprising:
generating reflection spectrum data indicative of a measurement of both an amplitude and a phase of a reflection for each core of the optical fiber as a function of wavelength, wherein the reflection spectrum data includes
unstrained reflection spectrum data indicative of a measurement of both the amplitude and the phase of the reflection for each core of the optical fiber as the function of wavelength in response to optical fiber having a reference shape, and
strained reflection spectrum data indicative of a measurement of both the amplitude and the phase of the reflection for each core of the optical fiber as the function of wavelength in response to optical fiber having a non-reference shape;
generating local strain data for each position of a plurality of positions along the optical fiber as a function of the reflection spectrum data, wherein generating the local strain data includes:
executing an inverse Fourier transforms of the reference reflection spectrum data and the reflection spectrum data with additional strain, and
calculating a phase difference between taper functions corresponding to the inverse Fourier transforms of the unstrained reflection spectrum data and the strained reflection spectrum data;
generating local curvature and torsion angle data at each position of the plurality of positions along the optical fiber as a function of corresponding local strain at each position of the plurality of positions along the optical fiber; and
reconstructing the 3D shape of the optical fiber as a function of the local curvature and torsion angle at each position of the plurality of positions along the optical fiber.

14. The method of claim 13, wherein the reconstruction of the 3D shape of the optical fiber includes a step size rotation of a local binormal axis of a curve over an angle equaling a product of the step size and curvature.

15. The optical shape sensing system of claim 14, wherein the reconstruction of the 3D shape of the optical fiber further includes:
a coordinate transformation of a local coordinate system to a reference coordinate system; and
calculating Jacobian matrix of the coordinate transformation for each step using the same rotation.

* * * * *